United States Patent
Wei et al.

(10) Patent No.: US 10,577,341 B1
(45) Date of Patent: Mar. 3, 2020

(54) BERAPROST-314D MONOHYDRATE CRYSTALS AND METHODS FOR PREPARATION THEREOF

(71) Applicant: CHIROGATE INTERNATIONAL INC., Yangmei, Taoyuan County (TW)

(72) Inventors: Shih-Yi Wei, Yangmei (TW); Jian-Bang Jheng, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 16/199,471

(22) Filed: Nov. 26, 2018

(51) Int. Cl.
*C07D 307/93* (2006.01)

(52) U.S. Cl.
CPC ........ *C07D 307/93* (2013.01); *C07B 2200/13* (2013.01)

(58) Field of Classification Search
CPC ................................................... C07D 307/93
USPC ......................................................... 549/458
See application file for complete search history.

(56) References Cited

U.S. PATENT DOCUMENTS

| 2012/0323025 A1* | 12/2012 | Sharma ................ C07D 307/93 549/458 |
| 2014/0275237 A1* | 9/2014 | Faulds ............... A61K 31/5585 514/468 |
| 2017/0166545 A1* | 6/2017 | Batra ................... C07D 307/93 |

FOREIGN PATENT DOCUMENTS

| CN | 103242274 B | * | 11/2014 | .......... C07D 307/93 |
| JP | 59134787 | * | 8/1984 | |
| KR | 1777632 | * | 9/2017 | |
| WO | WO-2012174407 A1 | * | 12/2012 | .......... C07D 307/93 |
| WO | WO-2017027706 A1 | * | 2/2017 | .......... C07D 307/93 |
| WO | WO-2017174439 A1 | * | 10/2017 | .......... C07D 307/93 |

OTHER PUBLICATIONS

Kobayashi; Beilstein J. Org. Chem. 2015, 11, 2654-2660. (Year: 2015).*
Wakita; Heterocycles 2000, 53, 1085-1110. (Year: 2000).*

* cited by examiner

*Primary Examiner* — Daniel R Carcanague
(74) *Attorney, Agent, or Firm* — Ladas & Parry LLP (57) ABSTRACT

The present invention provides a monohydrated form of Beraprost-314d, and a novel crystalline form of Beraprost-314d monohydrate, and processes for the preparation thereof.

14 Claims, 8 Drawing Sheets

BERAPROST-314D MONOHYDRATE CRYSTALS AND METHODS FOR PREPARATION THEREOF

FIELD OF THE INVENTION

The present invention relates in general to solid form of prostacyclin derivatives and in particular, to solid form of Beraprost-314d monohydrate and preparation methods thereof.

BACKGROUND OF THE INVENTION

Beraprost is a synthetic benzoprostacyclin analogue of natural prostacyclin consisting of four isomers (Beraprost-314d, Beraprost-314d's enantiomer, Beraprost-315d and Beraprost-315d's enantiomer), as shown in Scheme A. Among them, optically pure Beraprost -314d (termed Esuberaprost, APS-314d or BPS-314d) is the pharmacologically active isomer, and is currently under clinical trials as an added-on active pharmaceutical ingredient in the inhaled treprostinil (Tyvaso®) for the treatment of diseases such as pulmonary arterial hypertension in North America and Europe.

Scheme A

Beraprost-314d (BPS-314d)

Beraprost-314d's enantiomer

Beraprost-315d (BPS-315d)

Beraprost-315d's enantiomer

The anhydrous form of Beraprost-314d has been previously described, e.g., in Heterocycles, 2000, 53, 1085-1092, U.S. Pat. No. 8,779,170, and WO 2017/174439. According to the chemical structure feature of Beraprost-314d, an anhydrous Beraprost-314d molecule contains free active carbonyl acid functional groups, which can be easily esterified with hydroxyl functional groups of other anhydrous Beraprost-314d molecule to form a dimer at room temperature, and/or with alcohols contained in the residual solvents or excipients to form unwanted ester impurities in storage. Therefore, an anhydrous Beraprost-314d is not stable at room temperature and is unsuitable for storage, shipping, and formulation purposes at commercial considerations.

Beraprost-314d is of great importance from a pharmacologically point of view. Consequently, there is a demand for an efficient and economical preparation of a stable solid form of Beraprost-314d which presents advantages in storage, shipping, handling, and formulation.

SUMMARY OF THE INVENTION

Surprisingly, it has been found that Beraprost-314d can exist in a monohydrated form.

According to one aspect, the present invention relates to a monohydrated form of Beraprost-314d.

In one embodiment, the present invention provides a Beraprost-314d monohydrate having a 1% KBr Fourier transform infrared (FTIR) spectrum comprising peaks, in terms of $cm^{-1}$, at $3378\pm4$ $cm^{-1}$, $3200\pm4$ $cm^{-1}$, $3060\pm4$ $cm^{-1}$, $3020\pm4$ $cm^{-1}$, $2965\pm4$ $cm^{-1}$, $2923\pm4$ $cm^{-1}$, $2910\pm4$ $cm^{-1}$, $2887\pm4$ $cm^{-1}$, $2873\pm4$ $cm^{-1}$, $1710\pm4$ $cm^{-1}$, $1683\pm4$ $cm^{-1}$, $1593\pm4$ $cm^{-1}$, $1453\pm4$ $cm^{-1}$, $1375\pm4$ $cm^{-1}$, $1349\pm4$ $cm^{-1}$, $1304\pm4$ $cm^{-1}$, $1277\pm4$ $cm^{-1}$, $1254\pm4$ $cm^{-1}$, $1231\pm4$ $cm^{-1}$, $1196\pm4$ $cm^{-1}$, $1151\pm4$ $cm^{-1}$, $1099\pm4$ $cm^{-1}$, $1076\pm4$ $cm^{-1}$, $1036\pm4$ $cm^{-1}$, $1012\pm4$ $cm^{-1}$, $967\pm4$ $cm^{-1}$, $954\pm4$ $cm^{-1}$, $930\pm4$ $cm^{-1}$, $891\pm4$ $cm^{-1}$, $865\pm4$ $cm^{-1}$, $835\pm4$ $cm^{-1}$, $806\pm4$ $cm^{-1}$, $764\pm4$ $cm^{-1}$, $743\pm4$ $cm^{-1}$, and $667\pm4$ $cm^{-1}$.

In, one embodiment, the content of $4.33\pm2\%$ water in the hydrated form of Beraprost-314d obtained by Karl Fischer titration and thermogravimetric analysis (TGA) confirms that it is essentially a monohydrated form of Beraprost-314d.

According to one aspect, the present invention provides a crystalline Beraprost-314d monohydrate, which is stable at room temperature over a long period of time than the anhydrous Beraprost-314d.

According to one aspect, the present invention provides a crystalline monohydrate form of Beraprost-314d, termed Form A, having an X-ray powder diffraction (XRPD) pattern exhibiting its six strongest characteristic peaks at the following 2θ reflection angles: 6.1±0.2°, 12.1±0.2°, 13.9±0.2°, 16.9±0.2°, 19.4±0.2°, and 21.6±0.2°.

In one embodiment, the present invention provides a crystalline Beraprost-314d monohydrate Form A having a differential scanning calorimetry (DSC) thermogram pattern comprising two endothermic peaks with a peak onset temperature of about 50.5±1° C. and peak maximums of about 55.4±1° C. and 63.0±1° C.

According to one aspect, the present invention provides a crystalline monohydrate form of Beraprost-314d, termed Form B, having an XRPD pattern exhibiting its six strongest characteristic peaks at the following 2θ reflection angles: 6.5±0.2°, 13.0±0.2°, 18.2±0.2°, 19.0±0.2°, 20.1±0.2°, and 20.9±0.2°.

In one embodiment, the present invention provides a crystalline Beraprost-314d monohydrate Form B having a DSC thermogram pattern comprising two endothermic peaks with a peak onset temperature of about 50.9±1° C. and peak maximums of about 56.4±1° C. and 64.2±1° C.

In one embodiment, the crystalline form of Beraprost-314d monohydrate is Form A at a temperature of below 30±5° C. When temperature rises above 30° C., the crystalline Beraprost-314d monohydrate Form A converts slowly to a crystalline Beraprost-314d monohydrate Form B. When temperature declines below 30±5° C., the crystalline Beraprost-314d monohydrate Form B converts back to the original Form A. The crystalline form transformation of Beraprost-314d monohydrate between Form A and Form B is reversible.

According to one aspect, the present invention provides a method for preparing a crystalline Beraprost-314d monohydrate, which comprises dissolving Beraprost-314d in a first solvent selected from the group consisting of methanol, ethanol, propanol, butanol, acetonitrile, tetrahydrofuran, 1,4-dioxane, dimethyl sulfoxide, dimethylacetamide, dimethylformamide, and mixtures thereof to form a homogenous solution lowering the temperature and/or adding a second solvent of water to the homogenous solution; and stirring, until a precipitate is formed.

DETAILED DESCRIPTION OF THE INVENTION

Characterization of Monohydrated Form of Beraprost-314d

In the present invention, it has been surprisingly found that the Beraprost-314d can exist in a monohydrate form.

The characterization of the Beraprost-314d monohydrate was verified by the following processes:
1. Confirmation of the feature of hydrates by FTIR spectroscopy,
2. Determination of water content by Karl Fischer titration,
3. Determination of water content by TGA.

In one embodiment, the monohydrated form of Beraprost-314d has a 1% KBr Fourier transform infrared (FTIR) spectrum comprising peaks, in terms of $cm^{-1}$, at 3378±4 $cm^{-1}$, 3200±4 $cm^{-1}$, 3060±4 $cm^{-1}$, 3020±4 $cm^{-1}$, 2965±4 $cm^{-1}$, 2923±4 $cm^{-1}$, 2910±4 $cm^{-1}$, 2887±4 $cm^{-1}$, 2873±4 $cm^{-1}$, 1710±4 $cm^{-1}$, 1683±4 $cm^{-1}$, 1593±4 $cm^{-1}$, 1453±4 $cm^{-1}$, 1375±4 $cm^{-1}$, 1349±4 $cm^{-1}$, 1304±4 $cm^{-1}$, 1277±4 $cm^{-1}$, 1254±4 $cm^{-1}$, 1231±4 $cm^{-1}$, 1196±4 $cm^{-1}$, 1151±4 $cm^{-1}$, 1099±4 $cm^{-1}$, 1076±4 $cm^{-1}$, 1036±4 $cm^{-1}$, 1012±4 $cm^{-1}$, 967±4 $cm^{-1}$, 954±4 $cm^{-1}$, 930±4 $cm^{-1}$, 891±4 $cm^{-1}$, 865±4 $cm^{-1}$, 835±4 $cm^{-1}$, 806±4 $cm^{-1}$, 764±4 $cm^{-1}$, 743±4 $cm^{-1}$, and 667±4 $cm^{-1}$.

Figure 1:
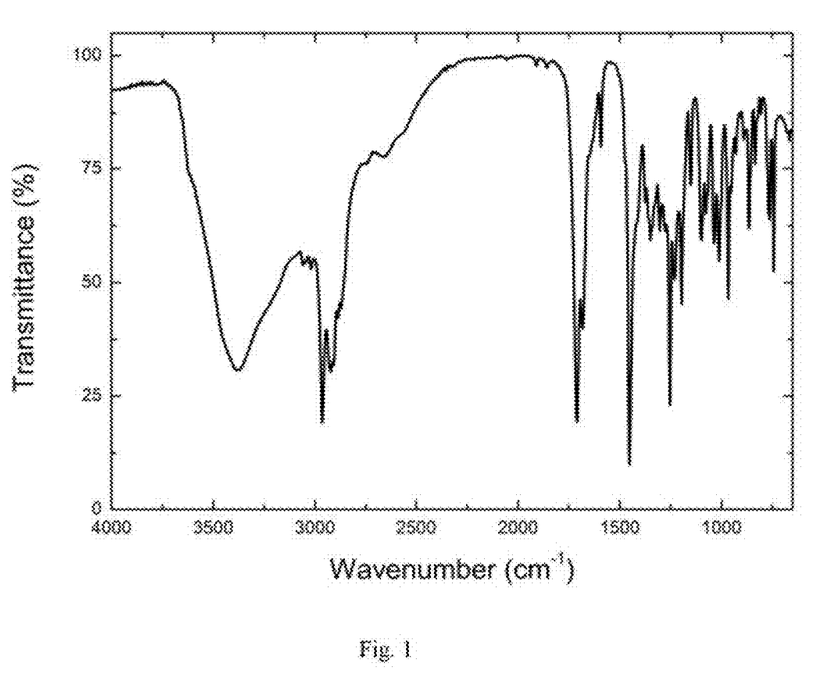
FIG. 1 shows a Fourier transform infrared (FTIR) spectrum of the monohydrated form of Beraprost-314d crystal.

In one embodiment, the present invention provides a crystalline Beraprost-314d monohydrate having a 1% KBr FTIR spectrum substantially as shown in FIG. 1.

Figure 2:
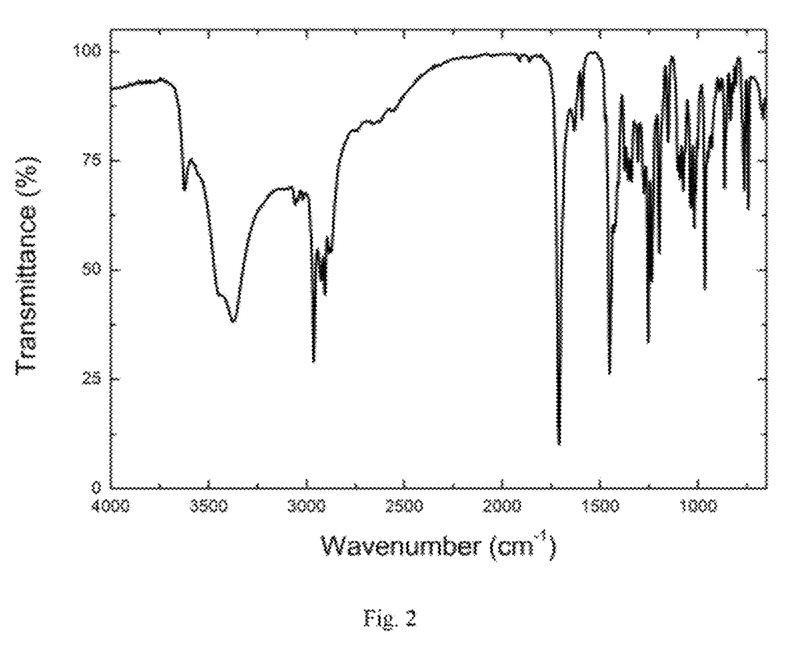
FIG. 2 shows a Fourier transform infrared (FTIR) spectrum of the anhydrous form of Beraprost-314d.

A comparison between the monohydrated and anhydrous forms of Beraprost-314d is presented in FTIR spectra, as shown in FIG. 1 and FIG. 2, respectively. The anhydrous form of Beraprost-314d was prepared by the method disclosed in U.S. Pat. No. 8,779,170. The FTIR feature peaks of the monohydrated form of Beraprost-314d crystal at about 3200±4 $cm^{-1}$ and about 1683±4 $cm^{-1}$ emphasize the feature of hydrates, indicating that the monohydrated form of Beraprost-314d is a distinct molecular entity.

The crystalline Beraprost-314d monohydrate obtained by the method of the present invention is essentially in a. monohydrated form, One mole of water molecule in Beraprost-314d was calculated to be about 4.33% by weight. The content of 4.33±2% water measured by Karl Fischer titration and thermogravimetric analysis (TGA) confirms that there is only one mole of water present in the hydrated form of Beraprost-314d for the Beraprost-314d monohydrate of the present invention.

The anhydrous Beraprost-314d is a fine, fly-away material having strong biological activity, which makes it difficult to avoid exposure during commercial handling. In the present invention, the monohydrated Beraprost-314d is much easier to weigh due to greatly reduced static electrical charge from the formation of Beraprost-314d monohydrate.

Therefore, the Beraprost-314d monohydrate f the present invention presents advantages in storage, shipping, handling, and formulation and can be widely and safely used for commercial purposes.

Crystalline Form of Beraprost-314d Monohydrate and Preparation Thereof

In one embodiment of the present invention, the method for preparing crystalline Beraprost-314d monohydrate comprises the steps of:

(a) dissolving crude Beraprost-314d in a first solvent selected from the group consisting of methanol, ethanol, propanol, butanol, acetonitrile, tetrahydrofuran, 1,4-dioxane, dimethyl sulfoxide, dimethylacetamide, dimethylformamide, and mixtures thereof to form a homogenous solution;

(b) lowering the temperature and/or adding a second solvent of water to the homogeneous solution;

(c) stirring until a precipitate is formed;

(d) filtering out the precipitate, thereby isolating the crystalline Beraprost-314d monohydrate; and (e) optionally drying the crystalline Beraprost-314d monohydrate.

The selection of the first solvent is the key to determine whether a crystalline Beraprost-314d monohydrate can be formed. In the present invention, the first solvent used to dissolve the crude Beraprost-314d is selected from the group consisting of methanol, ethanol, propanol, butanol, acetonitrile, tetrahydrofuran, 1,4-dioxane, dimethyl sulfoxide, dimethylacetamide, dimethylformamide, and mixtures thereof, preferably ethanol. The volume of the first solvent may be about 0.5 ml to about 100 ml, preferably about 1 ml to about 50 ml, and more preferably about 2 ml to about 25 ml, per 1 g of the crude Beraprost-314d. The crude Beraprost-314d can be dissolved in the first solvent at a temperature ranging from about 0° C. to about 80° C., preferably from about 10° C. to about 70° C., and more preferably from room temperature to about 60° C.

In one embodiment of the present invention, the temperature of the homogenous solution is lowered to a temperature ranging from about −30° C. to about 60° C., preferably from about −20° C. to about 50° C. and more preferably from about −10° C. to about 40° C.

In a preferred embodiment, the second solvent is water. The volume of the second solvent may he about 0.5 ml to about 20 ml, preferably about 1 ml to about 10 ml, and more preferably about 2 ml to about 5 ml, per 1 ml of the first solvent. The second solvent can be added at a temperature ranging from about −30° C. to about 60° C., preferably from about −20° C. to about 50° C., and more preferably from about −10° C. to about 40° C.

In one embodiment of the present invention, the precipitation of the crystal may be performed at a temperature ranging from about −30° C. to about 60° C., preferably from about −20° C. to about 50° C., and more preferably from about −10° C. to about 40° C.

In one embodiment of the present invention, the step of filtering out the precipitate comprises using the second solvent or a mixture of the first solvent and the second solvent to wash the precipitate. In the mixing solvent, the ratio of the first solvent and the second solvent may be about 1:1 to about 1:100, preferably about 1:2 to about 1:10.

Figure 3:
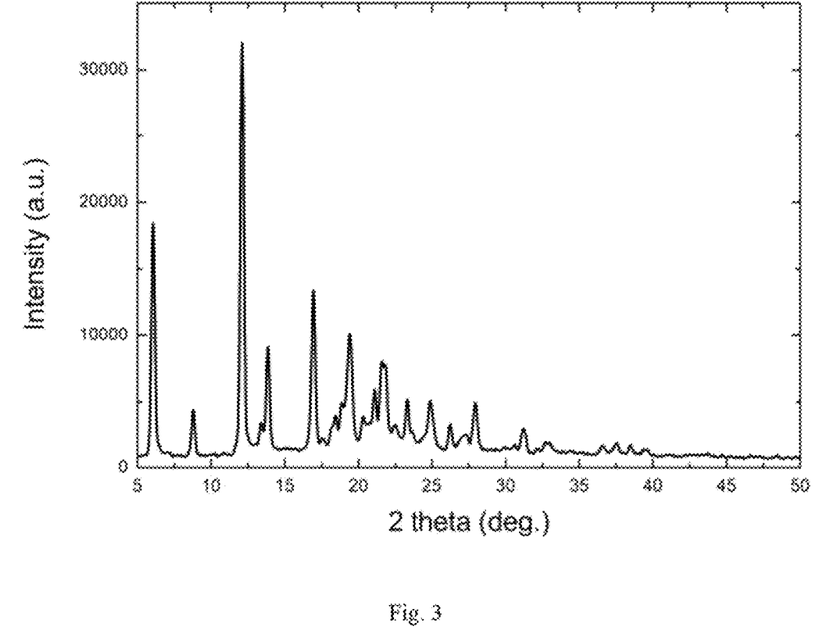
FIG. 3 shows an X-ray powder diffraction (XRPD) pattern of the crystalline Beraprost-314d monohydrate Form A.
Figure 4:
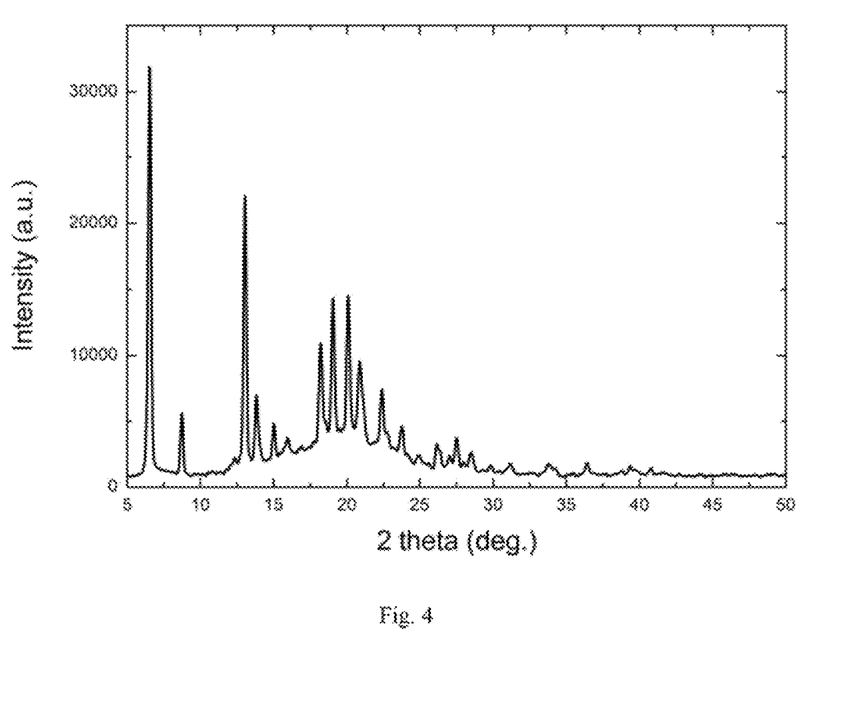
FIG. 4 shows an X-ray powder diffraction (XRPD) pattern of the crystalline Beraprost-314d monohydrate Form B.
Figure 5:
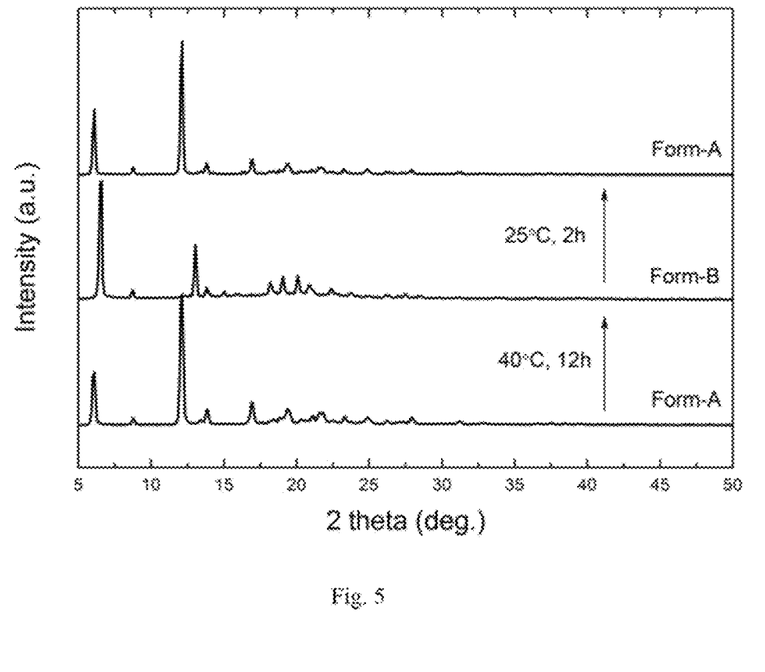
FIG. 5 shows a reversible crystalline form transformation between Form A and Form B of Beraprost-314d monohydrate crystal.

In the present invention, the crystalline form of Beraprost-314d monohydrate is selected from the group consisting of:

(a) Form A having an XRPD pattern exhibiting its six strongest characteristic peaks at the following 2θ reflection angles: 6.1±0.2°, 12.1±0.2°, 13.9±0.2°, 16.9±0.2°, 19.4±0.2°, and 21.6±0.2°;

(b) Form B having an XRPD pattern exhibiting its six strongest characteristic peaks at the following 2θ reflection angles: 6.5±0.2°, 13.0±0.2°, 18.2±0.2°, 19.0±0.2°, 20.1±0.2°, and 20.9±0.2°; and (c) a mixture thereof In one embodiment of the present invention, the Beraprost-314d monohydrate crystal shows an XRPD pattern feature termed Form A at temperature below 30±5° C., as shown in FIG. 3. When temperature rises above 30±5° C., the XRPD pattern of Beraprost-314d monohydrate crystal converts slowly to another feature termed Form B, as shown in FIG. 4. When the temperature declines below 30±5° C., the XRPD pattern of Beraprost-314d monohydrate crystal converts back to the original one termed Form A. The crystalline form transformation of Beraprost-314d monohydrate between Form A and Form B by increasing and decreasing temperature is reversible as shown in FIG. 5, and can be repeatedly performed more than five times.

The selection of the solvent and the precipitation temperature for preparing Beraprost-314d monohydrate crystal also affect the crystalline form of Beraprost-314d monohydrate during precipitation. For example, the pure Form A can be precipitated out by using ethanol and water as the first and second solvent at higher precipitation temperature (above 30±5° C.), however, Form A will convert slowly to Form B with time while kept at a higher precipitation temperature. On the other hand, the pure Form B can be precipitated out by using acetonitrile and water as the first and second solvent at a lower precipitation temperature (below 30±5° C.); nevertheless, Form B will convert to Form A with time while kept at the lower precipitation temperature.

In one embodiment of the present invention, the crystalline Beraprost-314d monohydrate Form A has an XRPD pattern exhibiting its six strongest characteristic peaks at the following 2θ reflection. angles: 6.1±0.2°, 12.1±0.2°, 13.9±0.2°, 16.9±0.2°, 19.4±0.2°, and 21.6±0.2°. In a preferred embodiment, the XRPD pattern further comprises characteristic peaks at the following 2θ reflection angles: 8.8±0.2°, 18.4±0.2°, 18.9±0.2°, 20.3±0.2°, 21.1±0.2°, 21.8±0.2°, 23.3±0.2°, 24.9±0.2°, and 28.0±0.2°. More preferably, the XRPD pattern of crystalline Beraprost-314d monohydrate Form A is consistent with FIG. 3. The particular data of crystalline Beraprost-314d monohydrate Form A are shown in Table 1.

TABLE 1

| 2θ angle (°) | d value(Å) | relative intensity (%) |
| --- | --- | --- |
| 6.1 | 14.6 | 56.4 |
| 8.8 | 10.1 | 11.5 |
| 12.1 | 7.3 | 100.0 |
| 13.4 | 6.6 | 8.1 |
| 13.9 | 6.4 | 76.5 |
| 16.9 | 5.2 | 39.9 |
| 17.6 | 5.0 | 4.4 |
| 18.4 | 4.8 | 9.9 |
| 18.9 | 4.7 | 12.8 |
| 19.4 | 4.6 | 29.4 |
| 20.3 | 4.4 | 9.6 |
| 21.1 | 4.2 | 16.1 |
| 21.6 | 4.1 | 22.9 |
| 21.8 | 4.1 | 71.1 |
| 22.5 | 4.0 | 7.6 |
| 23.3 | 3.8 | 13.8 |
| 73.6 | 3.8 | 6.0 |
| 24.9 | 3.6 | 13.4 |
| 26.2 | 3.4 | 7.9 |
| 27.3 | 3.3 | 5.2 |
| 78.0 | 3.2 | 13.1 |
| 31.2 | 2.9 | 6.7 |
| 37.7 | 2.7 | 3.6 |
| 33.0 | 2.7 | 3.3 |
| 36.6 | 2_5 | 1.7 |
| 37.5 | 2.4 | 3.4 |
| 38.5 | 2.3 | 3.0 |
| 39.4 | 2.3 | 1.9 |
| 39.6 | 2.3 | 1.9 |

In one embodiment, the present invention provides a crystalline Beraprost-314d monohydrate Form A having an XRPD pattern exhibiting its six strongest characteristic peaks at the following 2θ reflection angles: 6.1±0.2°, 12.1±0.2°, 13.9±0.2°, 16.9±0.2°, 19.4±0.2°, and 21.6±0.2°.

In one embodiment, the present invention provides a crystalline Beraprost-314d monohydrate Form A having an XRPD pattern substantially as shown in FIG. 3.

Figure 6:
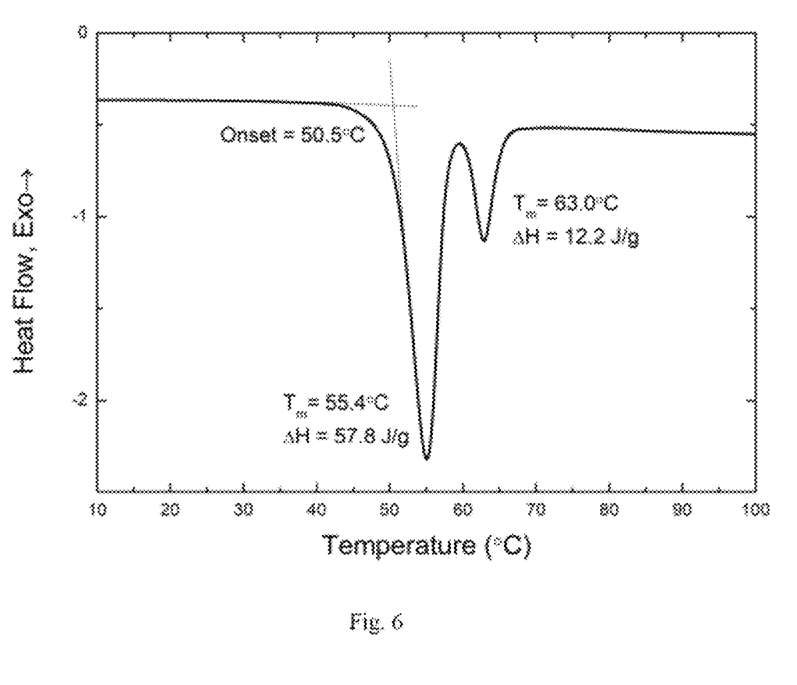
FIG. 6 shows a differential scanning calorimetry (DSC) thermogram pattern of the crystalline Beraprost-314d monohydrate Form A.

In one embodiment, the present invention provides a crystalline Beraprost-314d monohydrate Form A having a differential scanning calorimetry (DSC) thermogram pattern comprising two endothermic peaks with a peak onset temperature of approximately 50.5±1° C. and peak maximums of approximately 55.4°±1C and 63.0°±1C. In a preferred embodiment, the present invention, provides a crystalline Beraprost-314d monohydrate Form A having as DSC thermogram pattern substantially as shown in FIG. 6.

In one embodiment of the present invention, the crystalline Beraprost-314d monohydrate Form B has an XRPD pattern exhibiting its six strongest characteristic peaks at the following 2θ reflection angles; 6.5±0.2°, 13.0±0.2°, 18.2±0.2°, 19.0±0.2°, 20.1±0.2°, and 20.9±0.2°. In a preferred embodiment, the XRPD pattern further comprises characteristic peaks at the following 2θ reflection angles: 8.7±0.2°, 13.8±0.2°, 15.0±0.2°, 15.9±0.2°, 22.4±0.2°, 23.7±0.2°, 26.2±0.2°, 27.5±0.2°, and 28.5±0.2°. More preferably, the XRPD pattern of crystalline Beraprost-314d monohydrate Form B is consistent with FIG. 4. The particular data of crystalline Beraprost-314d monohydrate Form B are shown in Table 2.

TABLE 2

| 2θ angle (°) | d value (Å) | relative intensity (%) |
|---|---|---|
| 6.5 | 13.5 | 100.0 |
| 8.7 | 10.1 | 17.6 |
| 12.4 | 7.2 | 7.0 |
| 13.0 | 6.8 | 69.0 |
| 13.8 | 6.4 | 21.8 |
| 15.0 | 5.9 | 15.2 |
| 15.9 | 5.6 | 11.8 |
| 18.2 | 4.9 | 34.1 |
| 19.0 | 4.7 | 44.8 |
| 20.1 | 4.4 | 45.3 |
| 20.9 | 4.3 | 29.9 |
| 22.4 | 4.0 | 23.2 |
| 23.7 | 3.7 | 14.5 |
| 24.9 | 3.6 | 7.7 |
| 26.2 | 3.4 | 10.3 |
| 27.0 | 3.3 | 7.6 |
| 27.5 | 3.2 | 11.9 |
| 28.5 | 3.1 | 8.3 |
| 29.8 | 3.0 | 5.2 |
| 31.2 | 2.9 | 5.8 |
| 33.8 | 1.7 | 5.5 |
| 36.4 | 2.5 | 5.9 |
| 39.4 | 1.3 | 5.1 |
| 40.8 | 2.1 | 4.7 |

In one embodiment. the present invention provides a crystalline Beraprost-314d monohydrate Form B having an XRPD pattern exhibiting its six strongest characteristic peaks at the, following, 2θ reflection angles: 6.5±0.2°, 13.0±0.2°, 18.2±0.2°, 19.0±0.2°, 20.1±0.2°, and 20.9±0.2°.

In one embodiment, the present invention provides a crystalline Beraprost-314d monohydrate Form B having an XRPD pattern substantially as shown in FIG. 4.

In one embodiment, the present invention provides a crystalline Beraprost-314d monohydrate Form B having a DSC thermogram pattern comprising two endothermic peaks with a peak onset temperature of approximately 50.9±1° C. and peak maximum of approximately 56.4±1° C. and 64.2±1° C. In a preferred embodiment, the present invention provides a crystalline Beraprost-314d monohydrate Form B having a DSC thermogram pattern substantially as show in FIG. 7.

In the present invention, the content of 4.33±2% water in the crystalline Beraprost-314d monohydrate Form A and Form B measured by Karl Fischer titration and TGA indicates that the one mole of water was reserved in the hydrated form of Beraprost-314d during crystalline form transformation. Moreover, the changes of the FTIR feature peaks for Beraprost-314d monohydrate Form A and Form B appear invisible before and after crystalline form transformation.

EXAMPLES

X-ray Powder Diffraction (XRPD) Analysis: The XRPD patterns were collected on a Bruker D2 PHASER diffractometer with fixed divergence slits and 1D LYNXEYE detector. The samples (ca. 100 mg) were placed flat on a sample holder. The prepared samples were analyzed over a 2θ range from 5° to 50° with step size of 0.02 degrees and step time of 1 second using $CuK_\alpha$ radiation at a power of 10 mA and 30 kV The $CuK_\beta$ radiation was removed by a divergent beam nickel filter, Fourier Transform Infrared (FTIR) Analysis: The FTIR spectra were collected on a Perkin Elmer SPECTRUM 100 instrument, The samples were mixed with potassium bromide (KBr) in an approximately 1:100 ratio (w/w) using an agate mortar and pestle. The mixture was compressed in a pellet die at a pressure of about 10 to 13 tonnes for 2 minutes. The resulting disk was scanned 4 times versus a collected background from 4000 $cm^{-1}$ to 650 $cm^{-1}$ at a resolution of 4 $cm^{-1}$. The data were baseline corrected and normalized, Differential Scanning calorimetry (DSC) Analysis: The DSC patterns were collected on a TA DISCOVERY DSC25 instrument The samples (ca. 5 mg) were weighed into an aluminum pan with a crimping closed aluminum lid. The prepared samples were analyzed from 10° C. to 100° C. at scan rate of 10° C./min under a flow of nitrogen (ca. 50 ml/min). The melting temperature and heat of fusion were calibrated by indium (In) before measurement.

Example 1

Preparation of Crude Beraprost-314d

Methyl 4-((1R,2R,3aS,8bS)-2-hydroxy-1-((3S,4S,E)-3-hydroxy-4-methyloct-1-en-6-yn-1-yl)-2,3,3a,8b-tetrahydro-1H-cyclopenta[b]benzofuran-5-yl)butanoate (50.0 g, 121.2 mmol) was dissolved ethanol and followed in addition of 200 ml 1N sodium hydroxide/water solution and stirred at room temperature for 2 hour The reaction mixture was isolated by acid-base extraction, and the solvent was evaporated off under vacuum. The crude product purified by chromatography on silica gel using a mixture of hexane and ethyl acetate as a gradient eluent to obtain 33.2 g crude Beraprost-314d.

Example 2

Preparation of Anhydrous Beraprost-314d

The anhydrous Beraprost-314d was prepared by the m as disclosed in U.S. Pat. No. 8,779,170. Methyl 4-((1R,2R,3aS, 8bS)-2-hydroxy-1-((3S,4S,E)-3-hydroxy-4-methyloct-1-en-6-yn-1-yl)-2,3,3a,8b-tetrahydro-1H-cyclopenta[b]benzo-furan-5-yl)butanoate (1.00 g) was reacted in methanol and sodium hydroxide/water solution. The reaction mixture was isolated by acid-base extraction. The crude product was concentrated to evaporate residual solvent in vacuo to give 0.70 g anhydrous Beraprost-314d as foamy solid.

Example 3

Preparation of Crystalline Beraprost-314d Monohydrate Form A

Crude Beraprost-314d (10.00 g, from Example 1) and ethanol (10 ml) were heated at 40° C. for dissolution and then cooled to room temperature. Water (20 ml) was added slowly dropwise and the mixture was stirred in ice water bath for 18 hours until solid precipitation occurred. Afterwards, the resulting suspension was filtered and rinsed, and, then dried under high vacuum at room temperature for 24 hours to give 7.0 g crystalline Beraprost-314d monohydrate Form A. The XRPD and DSC results are the same as shown in FIG. 3 and FIG. 6.

Example 4

Preparation of Crystalline Beraprost-314d Monohydrate Form A

Crude Beraprost-314d (1.00 g, from Example 1) and methanol (10 ml) were heated at 40° C. for dissolution and then cooled to room temperature. Water (20 ml) was added slowly dropwise and the mixture was stirred for 18 hours until solid precipitation occurred. Afterwards, the resulting suspension was filtered and rinsed, and then dried under high vacuum at room temperature for 24 hours to give 0.62 g crystalline Beraprost-314d monohydrate Form A. The XRPD and DSC results are the same as shown in FIG. 3 and FIG. 6.

Example 5

Preparation of Crystalline Beraprost-314d Monohydrate Form A

Crude Beraprost-314d (0.30 g, from Example 1) and isopropyl alcohol (2.0 ml) were heated at 40° C. for dissolution and then cooled to roam temperature, Water (6.0 ml) was added slowly dropwise and the mixture was stirred in ice water bath for 18 hours until solid precipitation occurred, Afterwards the resulting suspension was filtered and rinsed, and then dried under high vacuum at room temperature for 24 hours to give 0.19 g crystalline Beraprost-314d monohydrate Form A. The XRPD and DSC results are the same as shown in FIG. 3 and FIG. 6.

Example 6

Preparation of Crystalline Beraprost-314d Monohydrate Form A

Crude Beraprost-314d (0.30 g, from Example 1) and methanol (1.5 ml) were heated at 40° C. for dissolution and then cooled to room temperature. Water (4.5 ml) was added slowly dropwise and the mixture was stirred in ice water bath for 18 hours until solid precipitation occurred. Afterwards, the resulting suspension was filtered and rinsed, and then dried under high vacuum at room, temperature for 24 hours to give 0.20 crystalline Beraprost-314d monohydrate Form A. The XRPD and DSC results are the same as shown in FIG. 3 and FIG. 6.

Example 7

Preparation of Crystalline Beraprost-314d Monohydrate Form A.

Crude Beraprost-314d (0.30 g, from Example 1) and dimethyl sulfoxide (0.6 ml) were heated at 40° C. for dissolution and then cooled to room temperature. Water (1.2 ml) was added slowly dropwise and the mixture was stirred for 48 hours until solid precipitation occurred. Afterwards, the resulting suspension was filtered and rinsed, and then dried under high vacuum at moot temperature for 24 hours to give 0.20 g crystalline Beraprost-314d monohydrate Form A. The XRPD and DSC results are the same as shown in FIG. 3 and FIG. 6.

Example 8

Preparation of Crystalline Beraprost-314d Monohydrate Form B

Figure 7:
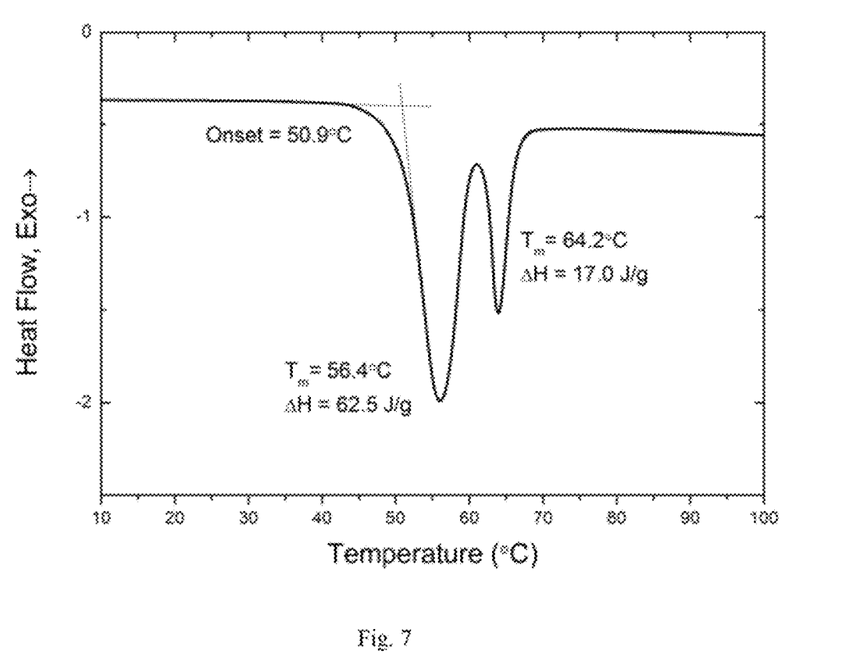
FIG. 7 shows a differential scanning calorimetry (DSC) thermogram pattern of the crystalline Beraprost-314d monohydrate Form B.

Crude Beraprost-314d (0.30 g, from Example 1) and acetonitrile (6 ml) were heated at 40° C. for dissolution and then cooled to room temperature. Water (12 ml) was added slowly dropwise and the mixture was stirred in ice water bath for 24 hours until solid precipitation occurred. Afterwards, the resulting suspension was filtered and rinsed, and then dried under high vacuum at room temperature for 24 hours to give 0.22 g crystalline Beraprost-314d monohydrate Form B. The XRPD and DSC results are the same as shown in FIG. 4 and FIG. 7.

Example 9

Preparation of Crystalline Beraprost-314d Monohydrate Form B

Crystalline Beraprost-314d monohydrate Form A (0.10 g, from Example 3) was placed in a glass vial, and heated at 35° C. and isothermal stood for 18 hours. Afterwards, the crystalline Beraprost-314d monohydrate Form A. was completely converted to crystalline Beraprost-314d monohydrate Form B. The XRPD and DSC results are the same as shown in FIG. 4 and FIG. 7.

Example 10

Preparation of Crystalline Beraprost-314d Monohydrate Form B

Crystalline Beraprost-314d monohydrate Form A (0.10 g, from Example 3) was placed in a glass vial, and heated at 40° C. and isothermal stood for 6 hours. Afterwards, the crystalline Beraprost-314d monohydrate Form A was completely converted to crystalline Beraprost-314d monohydrate Form B. The XRPD and DSC results are the same as shown in FIG. 4 and FIG. 7.

Example 11

Crystalline Form Transformation of Beraprost-314d Monohydrate Form A and Form B

The Beraprost-314d monohydrate crystal shows an XRPD patient feature termed Form A at temperature below 30±5° C., as shown in FIG. 3. When temperature raises above 30±5° C., the XRPD pattern of Beraprost-314d monohydrate crystal converts slowly to another feature termed Form B, as shown in FIG. 4. When the temperature declines below 30±5° C., the XRPD pattern of Beraprost-314d monohydrate crystal converts back to the original one termed Form A. The crystalline form transformation of Beraprost-314d monohydrate between Form A and Form B by increasing and decreasing temperature is reversible as shown in FIG. 5, and can be repeatedly perforated more than five times.

Figure 8:
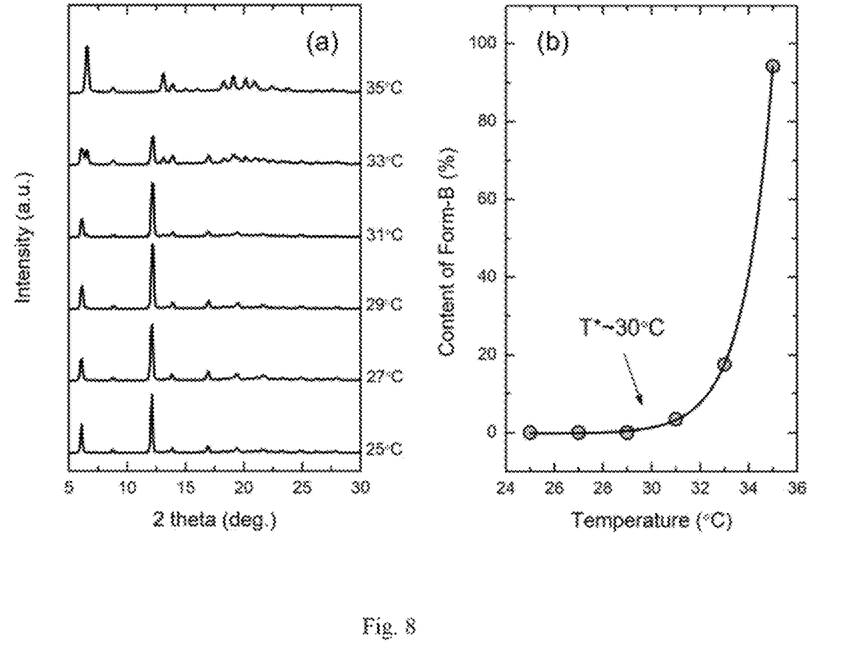
FIG. 8 shows (a) the crystalline form transformation of crystalline Beraprost-314d monohydrate from Form A to Form B during treatment at 25° C., 27° C., 29° C., 31° C., 33° C., and 35° C. for 24 hours, and (b) the content of crystalline Beraprost-314d monohydrate Form B converted from Form A during treatment at 25° C., 27° C., 29° C., 31° C., 33° C., and 35° C. for 24 hours.

The critical temperature (T*). of crystalline form transformation of Beraprost-314d monohydrate Form A and Form B was determined. Crystalline Beraprost-314d monohydrate Form A (0.10 g, from Example 3) was placed in glass vials, and heated to 25° C., 27° C., 29° C., 31° C., 33° C., and 35° C. and isothermal stood for 24 hours. The XRPD patterns of 31° C., 33° C., and 35° C. show an intermediate state containing both Form A and Form B during crystalline form transformation, as shown inn FIG. 8(a). The XRPD patterns of 25° C., 27° C. and 29° C. remain Form A without any Form B feature peaks, which indicate that crystalline form transformation of Beraprost-314d monohydrate from Form A to Form B took place only at temperature above 31° C. for 24 hours The content of Form B was calculated by peak resolved method from the XRPD patterns, as shown in FIG. 8(b). None of converted Form B was observed, indicating that the crystalline form transformation of Beraprost-314d monohydrate from Form A to Form B did not take place at temperature below the critical temperature of about 30±5° C.

Example 12

Stability of Anhydrous Form Versus Monohydrate Form of Beraprost-314d

The Beraprost-314d monohydrate is stable at room temperature. For example, the formation of dimer and/or unwanted esterification byproducts by the presence of hydrates can be avoided. About 0.10 g monohydrated form of Beraprost-314d (from Example 3) and the same amount of anhydrous form of Beraprost-314d (from Example 2) were placed respectively in glass vials, and isothermally stood at 40° C. for 3 days. The assay and total impurities of Beraprost-314d monohydrate and anhydrous Beraprost-314d were measured by HPLC after treatment at 40° C., as shown in Table 3. Stability data show that the monohydrated form of Beraprost-314d is more stable than the anhydrous form of Beraprost-314d. The assay of Beraprost-314d monohydrate showed no apparent decrease and the total impurities of Beraprost-314d monohydrate increased only 0.33% compared with the assay of anhydrous Beraprost-314d indicating that the Beraprost-314d monohydrate is more stable than the anhydrous Beraprost-314d at 40° C. for 3 days. Hence, the stability of Beraprost-314d was significantly improved due to the formation of Beraprost-314d monohydrate,

TABLE 3

| Specimen | Beraprost-314d Monohydrate | Beraprost-314d Monohydrate | Beraprost-314d Monohydrate |
|---|---|---|---|
| Conditions | 40° C./60% RH 1 day | 40° C./60% RH 2 days | 40° C./60% RH 3 days |
| Assay | 99.89% | 99.77% | 99.69% |
| Total Impurities | 0.17% | 0.25% | 0.33% |
| Specimen | Anhydrous Beraprost-314d | Anhydrous Beraprost-314d | Anhydrous Beraprost-314d |
| Conditions | 40° C./60% RH 1 day | 40° C./60% RH 2 days | 40° C./60% RH 3 days |
| Assay | 99.30% | 99.01% | 98.95% |
| Total Impurities | 0.84% | 1.13% | 1.19% |

What is claimed is:

1. A monohydrated form of Beraprost-314d.

2. The monohydrated for of Beraprost-314d of claim 1, which is in crystalline form.

3. The monohydrated form of Beraprost-314d of claim 2, wherein the crystalline form is Form A having an X-ray powder diffraction (XRPD) pattern exhibiting its six strongest characteristic peaks at the following 2θ reflection angles: 6.1±0.2°, 12.1±0.2°, 13.9±0.2°, 16.9±0.2°, 19.4±0.2°, and 21.6±0.2°.

4. The monohydrated form of Beraprost-314d of claim 3, wherein the XRPD pattern further comprises characteristic peaks at the following 2θ reflection angles: 8.8±0.2°, 18.4±0.2°, 18.9±0.2°, 20.3±0.2°, 21.1±0.2°, 21.8±0.2°, 23.3±0.2°, 24.9±0.2°, and 28.0±0.2°.

5. The monohydrated town, of Beraprost-314d of claim 4, wherein the XRPD pattern is substantially shown in FIG. 3.

6. The monohydrated form of Beraprost-314d of claim 3, having a differential scanning calorimetry (DSC) thermogram pattern comprising two endothermic peaks with a peak onset temperature of about 50.5±1° C. and peak maximums of about 55.4±1° C. and 63.0±1° C.

7. The monohydrated form of Beraprost-314d of claim 2, wherein the crystalline form is Form B having an XRPD pattern exhibiting its six strongest characteristic peaks at the following 2θ reflection angles: 6.5±0.2°, 13.0±0.2°, 18.2±0.2°, 19.0±0.2°, 20.1±0.2°, and 20.9±0.2°.

8. The monohydrated form of Beraprost-314d of claim 7, wherein the XRPD pattern further comprises characteristic peaks at the following 2θ reflection angles: 8.7±0.2°, 13.8±0.2°, 15.0±0.2°, 15.9±0.2°, 22.4±0.2°, 23.7±0.2°, 26.2±0.2°, 27.5±0.2°, and 28.5±0.2°.

9. The monohydrated form of Beraprost-314d of claim 8, wherein the XRPD pattern is substantially shown in FIG. 4.

10. The monohydrated form of Beraprost-314d of claim 7, having a DSC thermogram pattern comprising two endothermic peaks with a peak onset temperature of about 50.9±1° C. and peak maximums of about 56.4±1° C. and 64.2±1° C.

11. The monohydrated form of Beraprost-314d of claim 2, wherein the crystalline form is selected from the group consisting of
  (a) Form A having an X-ray powder diffraction (XRPD) pattern exhibiting its six strongest characteristic peaks at the following 2θ reflection angles: 6.1±0.2°, 12.1±0.2°, 13.9±0.2°, 16.9±0.2°, 19.4±0.2°, and 21.6±0.2°;
  (b) Form B having an XRPD pattern exhibiting its six strongest characteristic peaks at the following 2θ reflection angles: 6.5±0.2°, 13.0±0.2°, 18.2±0.2°, 19.0±0.2°, 20.1±0.2°, and 20.9±0.2°; and
  (c) a mixture thereof.

12. The monohydrated form of Beraprost-314d of claim 11, wherein the crystalline fora is Form A at a temperature of below 30±5° C., and the crystalline is Form B at a temperature of above 30±5° C.

13. A method for preparing a crystalline Beraprost-314d monohydrate, which comprises the steps of:

dissolving Beraprost-314d in a first solvent selected from the group consisting of methanol, ethanol, propanol, butanol, acetonitrile, tetrahydrofuran, 1,4-dioxane, dimethyl sulfoxide, dimethylacetamide, dimethylformamide, and mixtures thereof to form a homogenous solution;

lowering the temperature and/or adding, a second solvent, wherein the second solvent is water; and stirring until a precipitate is formed.

14. The method of claim 13, further comprising the steps of:

adding the second solvent or a mixture of the first solvent and the second solvent for rinsing the precipitate;

filtering out the precipitate; and optionally drying the precipitate.

* * * * *